(12) United States Patent
Wilk

(10) Patent No.: US 10,222,338 B1
(45) Date of Patent: Mar. 5, 2019

(54) APPARATUS AND METHOD OF DETECTING A MINERAL IN SOIL

(71) Applicant: Peter Wilk, New York, NY (US)

(72) Inventor: Peter Wilk, New York, NY (US)

(*) Notice: Subject to any disclaimer, the term of this patent is extended or adjusted under 35 U.S.C. 154(b) by 0 days.

(21) Appl. No.: 15/949,209

(22) Filed: Apr. 10, 2018

(51) Int. Cl.
*G01J 3/30* (2006.01)
*G01N 21/71* (2006.01)
*G01N 33/00* (2006.01)
*G01N 33/24* (2006.01)

(52) U.S. Cl.
CPC ....... *G01N 21/718* (2013.01); *G01N 33/0098* (2013.01); *G01N 33/24* (2013.01); *G01N 2201/06113* (2013.01); *G01N 2201/129* (2013.01)

(58) Field of Classification Search
CPC ........ G01J 3/28; G01J 3/44; G01J 3/02; G01J 3/00; G01N 21/71; G01N 33/00; G01N 33/24
See application file for complete search history.

(56) References Cited

U.S. PATENT DOCUMENTS

2007/0218556 A1* 9/2007 Harris .................. G01N 21/274 436/25
2008/0170218 A1* 7/2008 Dantus .................. G01N 21/65 356/39

* cited by examiner

*Primary Examiner* — Abdullahi Nur
(74) *Attorney, Agent, or Firm* — Nutter McClennen & Fish LLP

(57) ABSTRACT

A method of detecting a mineral or metal in soil causes at least a portion of a plant to burn to produce a light signature. The method also analyzes the light signature for the presence of the mineral or metal in the plant and determines if the light signature indicates the mineral or metal is present in the plant.

17 Claims, 6 Drawing Sheets

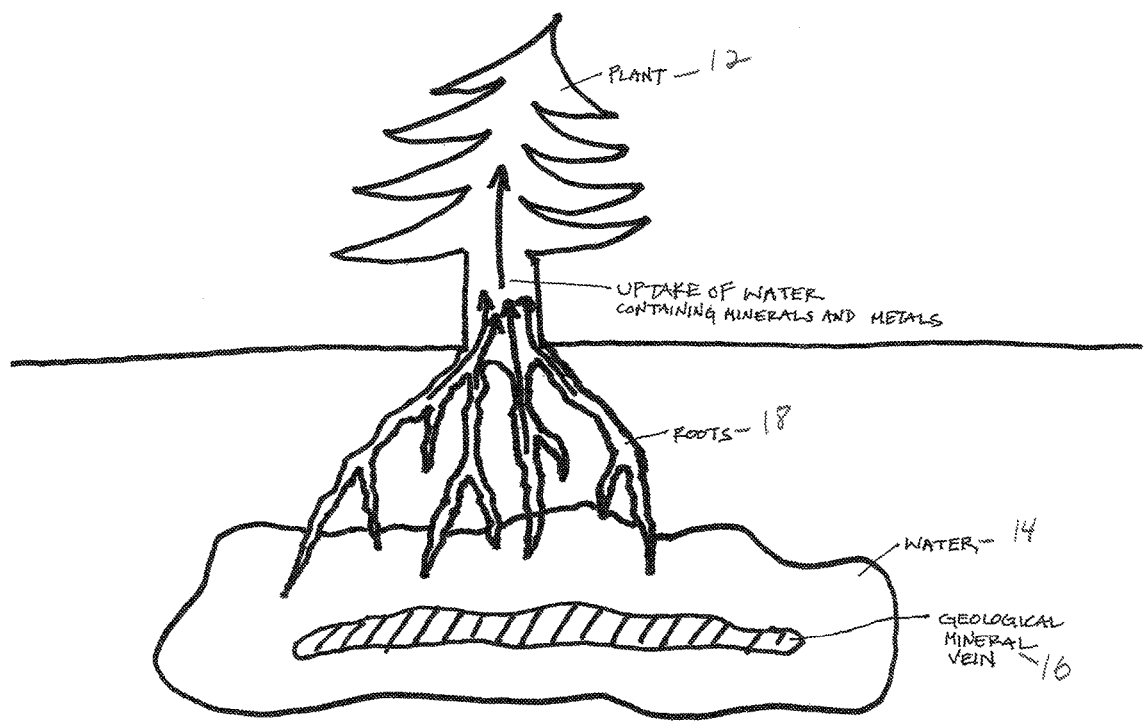

ately below.

APPARATUS AND METHOD OF DETECTING A MINERAL IN SOIL

FIELD OF THE INVENTION

Illustrative embodiments of the invention generally relate to mineral excavation and, more particularly, illustrative embodiments relate to locating mineral deposits.

BACKGROUND OF THE INVENTION

Geological veins are sheet-like formations of crystallized minerals found within rock. Geological veins form within rock as water carries these minerals through the ground, depositing them within the rock. The mineral deposits of geological veins often include precious metals, such as gold, silver, ruthenium, rhodium, palladium, osmium, uranium, and iridium, as well as other valuable metals, such as manganese and magnesium.

Due to their nature, most geological veins lay underground and their detection from aboveground remains difficult. Determining whether a geological vein possesses valuable metals requires costly excavation and extraction of the mineral deposit, followed by laboratory testing.

SUMMARY OF VARIOUS EMBODIMENTS

In accordance with one embodiment of the invention, a method of detecting a mineral or metal in soil causes at least a portion of a plant to burn to produce a light signature. The method also analyzes the light signature for the presence of the mineral or metal in the plant and determines if the light signature indicates the mineral or metal is present in the plant.

The light signature may be detected using spectroscopy and the mineral or metal may be gold, silver, ruthenium, rhodium, palladium, osmium, iridium, magnesium, or manganese. A user causes the plant to burn by directing an energy source onto at least a portion of the plant. The energy source may be a microwave, or a laser, and may be directed to at least a portion of the plant using a handheld device. Among other ways, the energy source is directed to the at least a portion of the plant while flying over the plant.

In accordance with another embodiment of the invention, an apparatus for detecting a mineral or metal includes an energy source that is able to cause at least a portion of a plant to burn to produce a light signature. The apparatus also includes logic configured to analyze the light signature for the presence of the mineral or metal in the plant and to determine if the light signature indicates that the mineral or metal is present in the plant. Additionally, the apparatus includes a spectroscope that is configured to determine if the light signature is indicative of the mineral or metal of interest.

The apparatus may also be coupled to an aircraft, such as a helicopter, airplane, drone, autogyro, air balloon, or blimp, a hand-held device, or a land-based movable device (e.g., an automobile or similar device).

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 2 schematically shows an exemplary cross-section of a plant growing above a geological mineral vein.

DESCRIPTION OF ILLUSTRATIVE EMBODIMENTS

In illustrative embodiments, an apparatus and method detects underground geological veins containing minerals, including metals. To that end, illustrative embodiments interrogate plants above underground geological mineral veins for the presence of at least trace amounts of the desired minerals. A plant preferably is interrogated by transforming it; in this case, directing an energy source to at least a portion of the plant, causing it to burn. The spectrum of light emitted by the burning plant then is analyzed for the spectral signature of the mineral of interest. Detection of the spectral signature of the mineral of interest indicates that a geological vein possessing the mineral or metal of interest likely lies underneath or near the interrogated plant. Details of illustrative embodiments are discussed below.

Geological mineral veins typically lie underground and the detection of underground geological veins comprising specific minerals remains technically difficult without excavation of the land. Undesirably, land excavation can be costly, particularly due to the somewhat speculative nature of mineral exploration. Current technology known to the inventor cannot efficiently solve this problem. The inventor recognized this technical problem and discovered a different, more efficient technology for locating minerals. One such embodiment is described below.

Figure 1:
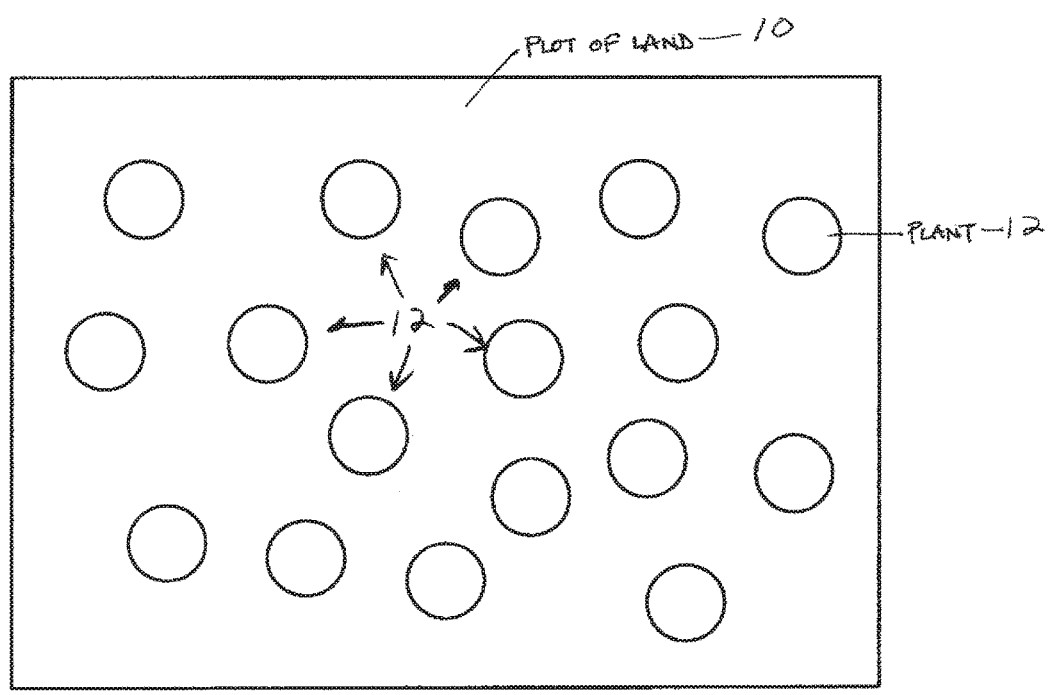
FIG. 1 schematically shows a plot of land that may be analyzed for underground geological mineral veins containing a mineral or metal of interest.

FIG. 1 schematically shows a plot of land 10 that may be analyzed for underground geological mineral veins 16 containing a mineral or metal of interest. It should be expressly noted that unless expressly noted otherwise, the term "mineral" is used herein to include metals. Open circles on the figure denote plants 12 that lie aboveground and which will be interrogated using the methods described below. A person of ordinary skill in the art will appreciate that a plant 12 is multicellular eukaryotic organism belonging to the kingdom Plantae.

FIG. 2 shows a cross-sectional view of an exemplary plant 12 growing above a geological mineral vein 16. Indeed, this figure is schematic and intended merely to illustrate an example of one application of various embodiments. The figure shows a pool 14 of water around a subterranean vein 16 of minerals. The inventor recognized that as water gathers beneath the ground around the geological mineral vein 16, some of the mineral may leech or migrate into the water. As such, the water may consequently have trace or larger concentrations of the mineral in the vein 16. Roots 18 of the noted plant 12, which grows above or near this mineral vein 16, may take up or otherwise absorb this underground water in its normal course. Accordingly, when the plant's roots 18 take up this water, it also takes up the trace or other concentrations of minerals in the water. The plant 12 consequently assimilates and distributes these absorbed minerals throughout its body. As such, the mineral may be present in many parts of the plant 12, such as its leaves, stems, and branches. The inventor recognized that this distribution of the trace mineral could be used to more efficiently and effectively identify the location of the vein 16 of minerals beneath the surface of the ground.

Figure 3A:
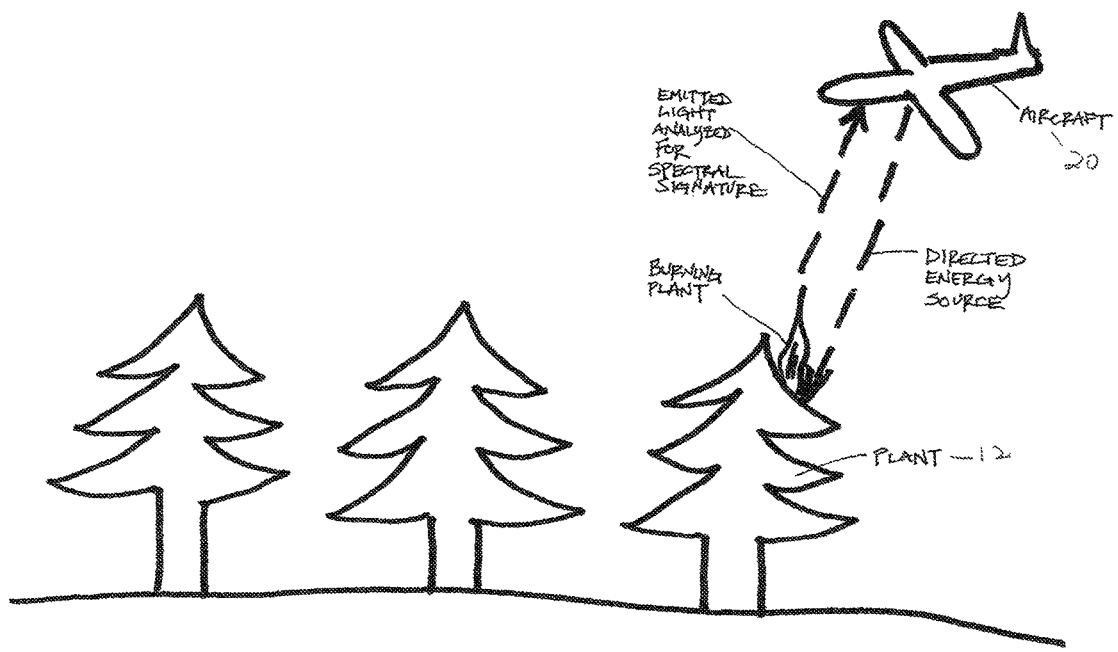
FIG. 3A schematically shows the detection of a specific metal or mineral of interest in a plant using a device present on an aircraft in accordance with illustrative embodiments.

FIG. 3A schematically shows one technique to detect a specific mineral of interest in accordance with one embodiment of the invention. The mineral or metal of interest may be any mineral or metal that may be taken up by plants 12, such as gold, silver, ruthenium, rhodium, palladium, osmium, iridium, magnesium, uranium, or manganese. The technique utilizes an energy device 28 capable of directing energy toward at least a portion of a plant 12 with an amplitude sufficient to burn at least a portion of the plant 12. As discussed below, the technique analyzes the spectral signature of the burning plant 12 to detect trace amounts of the mineral.

FIG. 3A shows one exemplary modality for performing this technique—using an overhead device, such as a plane 20. Indeed, overhead modalities may include any of a wide variety of conventional devices, such as the airplane 20 (as shown in the figure), and this airplane 20 can be piloted or a drone. Other examples include balloons, gliders, helicopters, autogyros, airships, or blimps.

Various embodiments are not limited to flying devices. For example, some embodiments may implement this modality using a handheld device operated by a user on the ground. Other embodiments envision underwater or waterproof devices to interrogate underwater plants 12 (not shown). For example, a diver holding a handheld device may interrogate underwater plants 12. Alternatively, the modality may be part of a boat or submersible, such as a manned or unmanned submarine.

The energy device 28 is configured to direct energy from its energy source toward at least a portion of a plant 12 in a manner that causes the plant 12 to transform in a prescribed manner. In illustrative embodiments, this transformation occurs when the portion of the plant 12 burns. The energy device 28 may generate energy in a variety of forms, such as via microwave or laser energy. In certain embodiments, associated logic is configured to read the spectral signature of the burning plant 12 matter. As known by those in the art, the spectral signature is a measurement of the intensity of light over a specific portion of the electromagnetic spectrum. Preferably, the measured portion of the electromagnetic spectrum ranges from about 320 nm to about 1000 nm in wavelength. Among other things, this spectral signature may be read using an optical spectrometer, spectrophotometer, spectrograph, or spectroscope.

To detect the presence or absence of a mineral in a plant 12, illustrative embodiments compare the spectral signature of the emitted light to the known spectral signature of one or more of a plurality of different minerals. For example, some embodiments may compare the spectral signature of the emitted light against spectral signatures of gold and magnesium to determine if a gold or magnesium vein 16 is beneath the plant 12. A match between the detected spectral signature and the known spectral signature indicates the presence of the mineral or metal of interest in the plant 12 and is evidence of a geological mineral vein 16 containing the mineral or metal of interest lying underneath or near the plant 12. This process may then be repeated on other plants 12 nearby to map out the approximate location/area of an underground geological mineral vein 16 that contains the mineral or metal of interest.

Figure 3B:
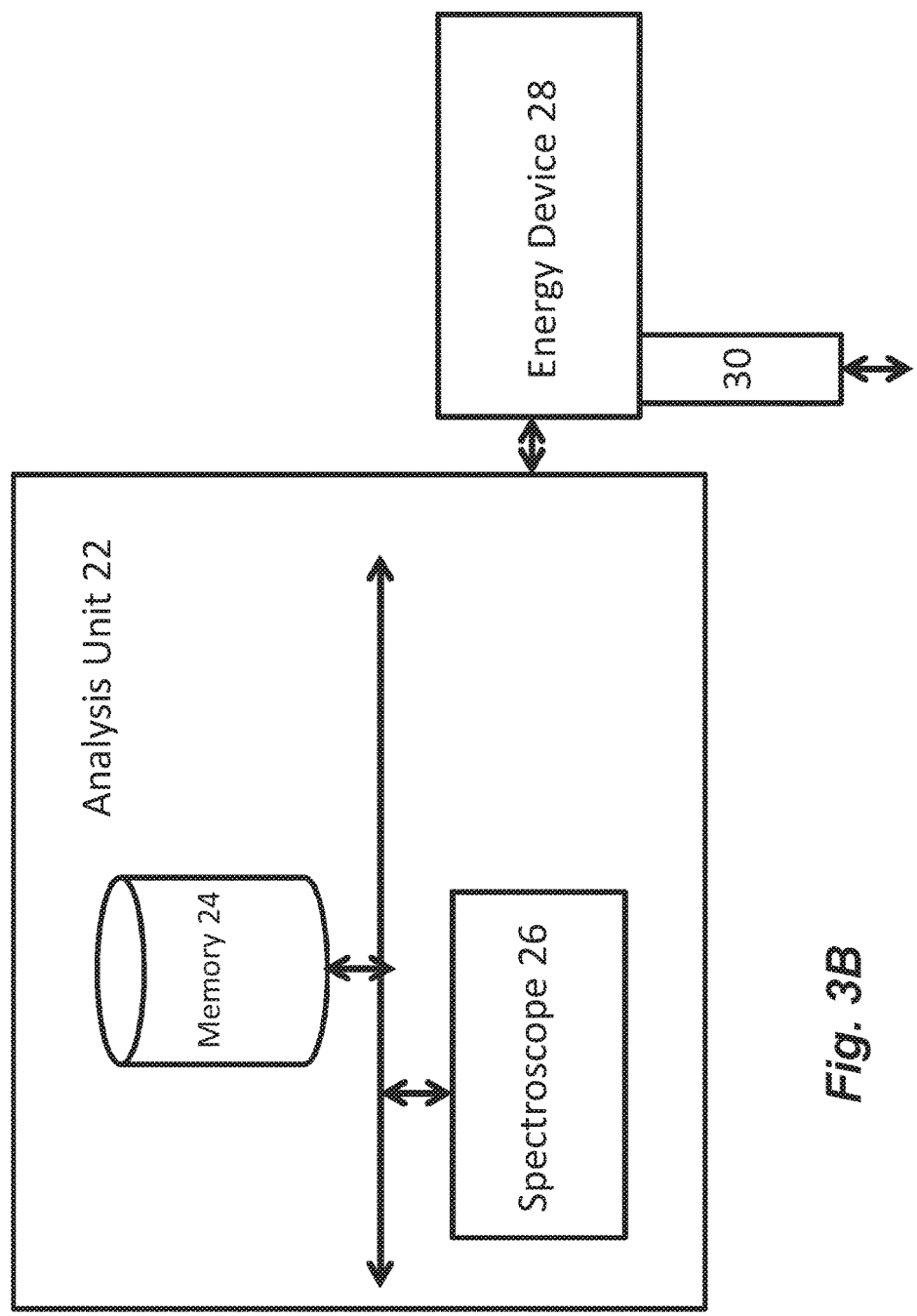
FIG. 3B schematically shows details of a system for detecting the presence of a mineral or metal in accordance with illustrative embodiments of the invention.

FIG. 3B schematically shows more details of a system for detecting the presence of a mineral or metal in accordance with illustrative embodiments. Each of the components of this figure is operatively connected by any conventional interconnect mechanism. FIG. 3B simply shows a bus communicating each the components. Those skilled in the art should understand that this generalized representation can be modified to include other conventional direct or indirect connections. Accordingly, discussion of a bus is not intended to limit various embodiments.

Indeed, it should be noted that FIG. 3B only schematically shows each of these components. Those skilled in the art should understand that each of these components can be implemented in a variety of conventional manners, such as by using hardware, software, or a combination of hardware and software, across one or more other functional components. For example, the spectrometer may be implemented using a plurality of microprocessors executing firmware. As another example, the spectrometer may be implemented using one or more application specific integrated circuits (i.e., "ASICs") and related software, or a combination of ASICs, discrete electronic components (e.g., transistors), and microprocessors. Accordingly, the representation of the spectrometer and other components in a single box of FIG. 3B is for simplicity purposes only. In fact, in some embodiments, the spectrometer of FIG. 3B is distributed across a plurality of different machines—not necessarily within the same housing or chassis.

It should be reiterated that the representation of FIG. 3B is a significantly simplified representation. Those skilled in the art should understand that such a device may have many other physical and functional components, such as central processing units, other data processing modules, and short-term memory. Accordingly, this discussion is in no way intended to suggest that FIG. 3B represents all of the elements of a system for detecting a mineral or metal.

As shown, the system includes an analysis unit 22 having memory 24 operatively coupled with a spectroscope 26. Those skilled in the art may select an appropriate type of spectroscope 26 for the task at hand. The memory 24 may store sample data for spectral signatures of various metals and minerals, and output data from the process of FIG. 4 (discussed below). The analysis unit 22 is operatively coupled with an energy device 28 having an interface for directing energy toward a plant 12 and receiving a signal representative of the light signature of a burning plant 12.

Figure 4:
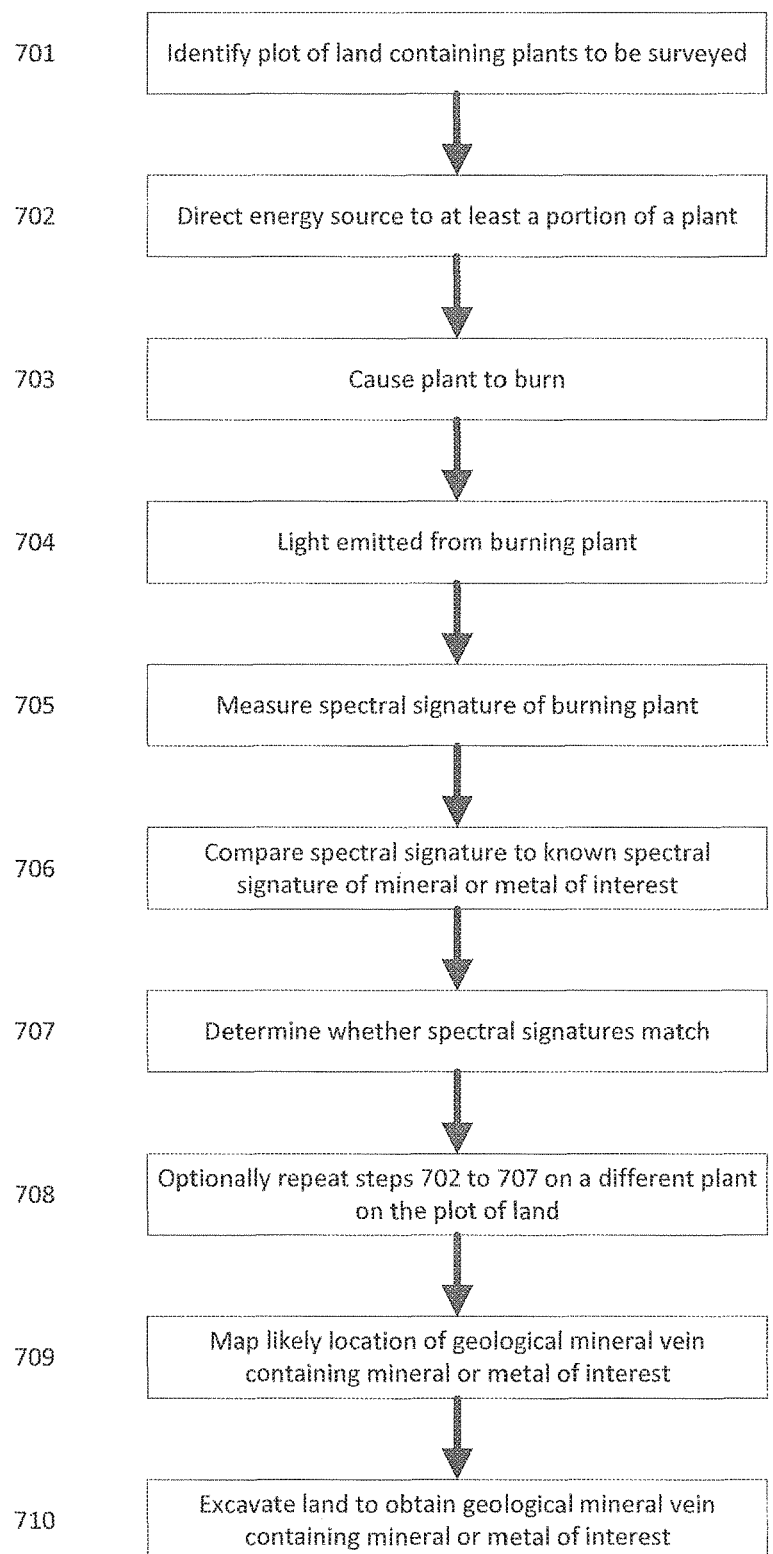
FIG. 4 shows a process of detecting the geological mineral vein in accordance with illustrative embodiments.

FIG. 4 shows a method detecting a mineral vein 16 in accordance with illustrative embodiments of the invention. It should be noted that this process is substantially simplified from a longer process that normally may be used to locate the mineral vein 16. Accordingly, the process of locating the mineral vein 16 may have many steps, such as testing steps or extraction steps, which those skilled in the art may use. In addition, some of the steps may be performed in a different order than that shown, or at the same time. Those skilled in the art therefore can modify the process as appropriate. Moreover, as noted above and below, many of the devices and structures noted are but one of a wide variety of different devices and structures that may be used. Those skilled in the art can select the appropriate devices and structures depending upon the application and other constraints. Accordingly, discussion of specific devices and structures is not intended to limit all embodiments.

The method begins at step 701, which identifies a plot of land 10 for surveying. The plot of land 10 ideally has sufficient plant growth such that more than one plant 12 on the land can be transformed and interrogated. Next, at step 702, a device directs energy toward at least a portion of a plant 12 on the plot of land 10. This energy source may be any energy source capable of causing plant matter to transform and generate light. In illustrative embodiments, this transformation the plant 12 burning in a controlled or uncontrolled manner. Preferably, as noted above, the energy source is a microwave or a laser delivered by some modality. One skilled in the art must be careful, however, to send a sufficient amount of energy to burn the plant 12, but not cause a larger fire, which undesirably could cause widespread damage. Some embodiments therefore may have personnel on the ground, near the burning plant 12, to ensure that the burning plant 12 does not cause a larger fire. Other embodiments may take precautions in the vicinity of the plant 12, such as materials and mechanisms to avoid the uncontrolled spread of fire.

After sufficient energy has been directed toward at least a portion of the plant 12, the plant 12 begins to burn, as depicted in step 703. The burning plant 12 emits light in step 704, and an optical device then measures the emitted light at step 705. Among other things, as noted above, the optical device may include an optical spectrometer, spectrophotometer, spectrograph, or, a spectroscope. The spectral signature of the emitted light is anticipated to read from about 320 nm to about 1000 nm, although other ranges may be used. Step 706 then compares the measured spectral signature to the known spectral signature of one or more minerals of interest, such as gold, silver, ruthenium, rhodium, palladium, osmium, iridium, uranium, magnesium, or manganese. Step 707 then determines whether the spectral signatures match a known spectral signature of a mineral or metal of interest. If the spectral signatures do match, this indicates that the mineral of interest is present in the plant 12, which is highly likely to be evidence of a geological mineral vein 16 containing the mineral of interest underground, beneath, or near the plant 12.

In step 708, this process is optionally repeated on at least one other plant 12 lying on the plot of land 10. After carrying out this process on one or plants 12 on the plot of land 10, illustrative embodiments generate a map 32 of the potential location of the geological mineral vein 16 based on the results of the spectral analysis (step 709). As noted, plants 12 that produced spectral signatures matching the known spectral signature of the mineral of interest are likely to have a geological mineral vein 16 containing the mineral of interest running underground beneath or near them. Conversely, plants 12 that did not produce spectral signatures matching the known spectral signature of the mineral of interest are unlikely to have a geological mineral vein 16 containing the mineral of interest running underground beneath or near them. Based on this information, illustrative embodiments generate a map 32 of the approximate location of the geological mineral vein 16, which subsequently can be excavated in step 710 to extract the mineral of interest from the geological mineral vein 16.

Figure 5:
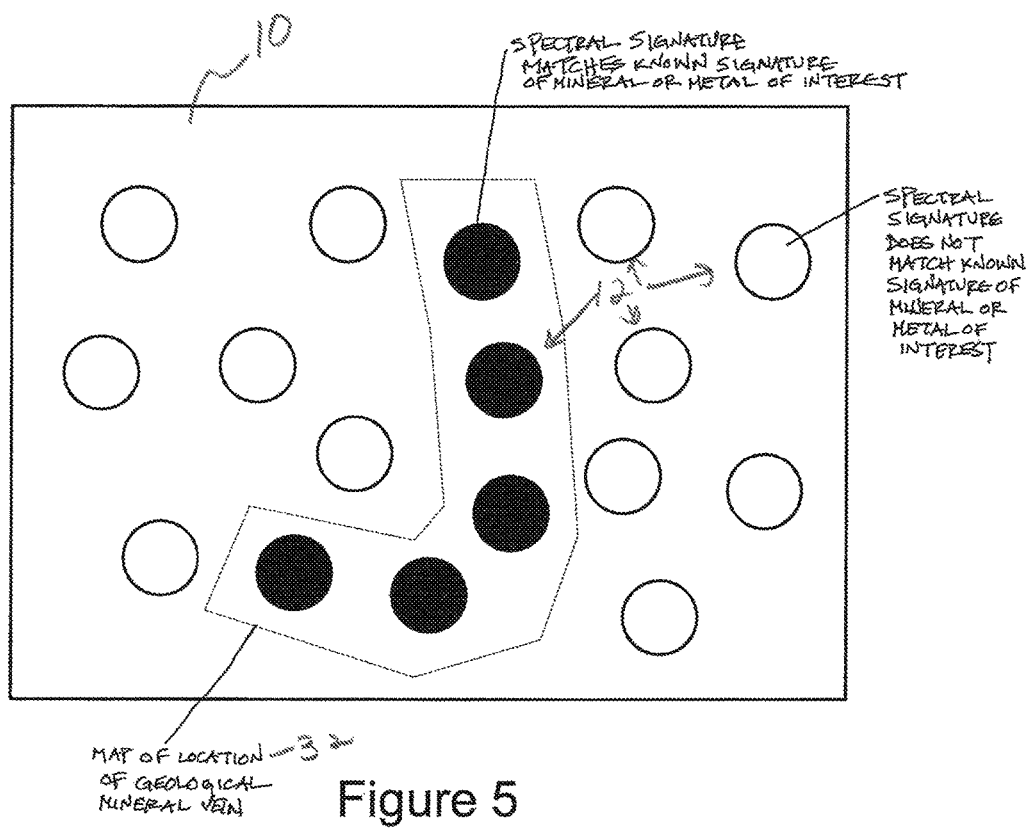
FIG. 5 shows an exemplary plot of land that has been analyzed for the presence of a geological mineral vein using the method of FIG. 4.

FIG. 5 shows an exemplary plot of land 10 that has been analyzed by the method described above. Plants 12 that produced spectral signatures matching the known spectral signature of the mineral of interest are depicted by black-filled circles. Plants 12 that did not produced spectral signatures matching the known spectral signature of the mineral of interest are depicted by open circles. Based on this information, a the probable location of a geological mineral vein 16 containing the mineral of interest is determined, as depicted by the area within the dotted line. This area can then be excavated to extract the mineral vein 16 containing the mineral of interest.

Alternative embodiments avoid the need for the above noted modalities for delivering the energy, and the in-situ burning. Specifically, such embodiments envision collection vegetation (e.g., retrieving leaves using clippers, scissors, or other known mechanism), marking the location of the collected vegetation (e.g., on the leaves themselves and/or at the site), and performing the burning and spectral analysis at another site. This other site may include, among other places, a laboratory in the field or at a sophisticated analysis location. In fact, this alternative embodiments may perform the burning and spectral analysis at the site after collecting the vegetation.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A method of locating a mineral or metal in soil, the method comprising:
   transforming a plant rooted on a plot of land by causing at least a portion of the plant to burn to produce a light signature;
   analyzing the light signature for the presence of the mineral or metal in the plant; and
   determining that the light signature indicates the mineral or metal is present in the plant.

2. The method of claim 1 wherein the light signature is detected using spectroscopy.

3. The method of claim 1 wherein the mineral or metal is selected from the group consisting of gold, silver, ruthenium, rhodium, palladium, osmium, iridium, magnesium, and manganese.

4. The method of claim 1 wherein transforming the plant comprises directing an energy source onto the at least a portion of the plant while the plant is rooted in the plot of land.

5. The method of claim 4 wherein the energy source is a microwave device, or a laser.

6. The method of claim 4 wherein the energy source is directed to the at least a portion of the plant using a handheld device.

7. The method of claim 4 wherein the energy source is directed to the at least a portion of the plant while flying over the plant.

8. An apparatus for detecting a mineral or metal, the apparatus comprising:
   an energy source capable of transforming a plant rooted on a plot of land by causing at least a portion of the plant to burn to produce a light signature;
   a spectroscope configured to analyze the light signature and determine whether the light signature is indicative of the mineral or metal.

9. The apparatus of claim 8 wherein the mineral or metal is selected from the group consisting of gold, silver, ruthenium, rhodium, palladium, osmium, iridium, magnesium, and manganese.

10. The apparatus of claim 8 wherein the energy source is a microwave device or a laser.

11. The apparatus of claim 8 wherein the apparatus is handheld.

12. The apparatus of claim 8 wherein the apparatus is configured to be coupled to an aircraft.

13. The apparatus of claim 12 wherein the aircraft is a helicopter, airplane, drone, autogyro, air balloon, or blimp.

14. The apparatus of claim 8 wherein the spectroscope includes a comparator to compare the light signature to a known light signature of the mineral or metal.

15. A computer program product for use on a computer system for locating a mineral or metal in soil, the computer program product comprising a tangible, non-transient computer usable medium having computer readable program code thereon, the computer readable program code comprising:
   program code for transforming a plant rooted on a plot of land by directing an energy source toward at least a portion of the plant causing the at least a portion of the plant to burn and produce a light signature;
   program code for analyzing the light signature for the presence of the mineral or metal in the plant; and
   program code for determining that the light signature indicates the mineral or metal is present in the plant.

16. The computer program product of claim 15 wherein the light signature is detected using spectroscopy.

17. The computer program product of claim 15 wherein the mineral or metal is selected from the group consisting of gold, silver, ruthenium, rhodium, palladium, osmium, iridium, magnesium, and manganese.

* * * * *